United States Patent [19]

Chang

[11] Patent Number: 5,390,230
[45] Date of Patent: Feb. 14, 1995

[54] CONTROLLED ATMOSPHERE, VARIABLE VOLUME SAMPLE HOLDER FOR X-RAY DIFFRACTOMER

[75] Inventor: On-Kok Chang, San Jose, Calif.

[73] Assignee: Valence Technology, Inc., San Jose, Calif.

[21] Appl. No.: 40,058

[22] Filed: Mar. 30, 1993

[51] Int. Cl.6 .......................................... G01N 23/20
[52] U.S. Cl. ........................................ 378/80; 378/79
[58] Field of Search ................................. 378/79, 80

[56] References Cited

U.S. PATENT DOCUMENTS 5,084,910 1/1992 Albe et al. .......................... 378/79
5,181,233 1/1993 Rink et al. .......................... 378/79

Primary Examiner—Craig E. Church
Attorney, Agent, or Firm—S. Russell LaPaglia

[57] ABSTRACT

A sample holder for diffraction analysis protects air or moisture sensitive samples and accommodates samples of different sizes, both without contributing to background noise. In particular, a sample holder for beam diffractometery includes a holder body having a substantially flat beam-facing top surface and a through-hole extending through the top surface, a piston fitted in the through-hole so as to travel along an axis of the through-hole, and a cup-shaped cap fitted over at least a portion of the top surface, surrounding the through-hole. To minimize background noise, the top surface of the holder body and a top surface of the piston are made of quartz. For sample loading, a substantially flat plate and a mechanism for removably attaching the plate so as to overlie the top surface of the holder body are provided. The cap may be made of thin plastic so as to not affect the incident X-ray beam.

9 Claims, 2 Drawing Sheets

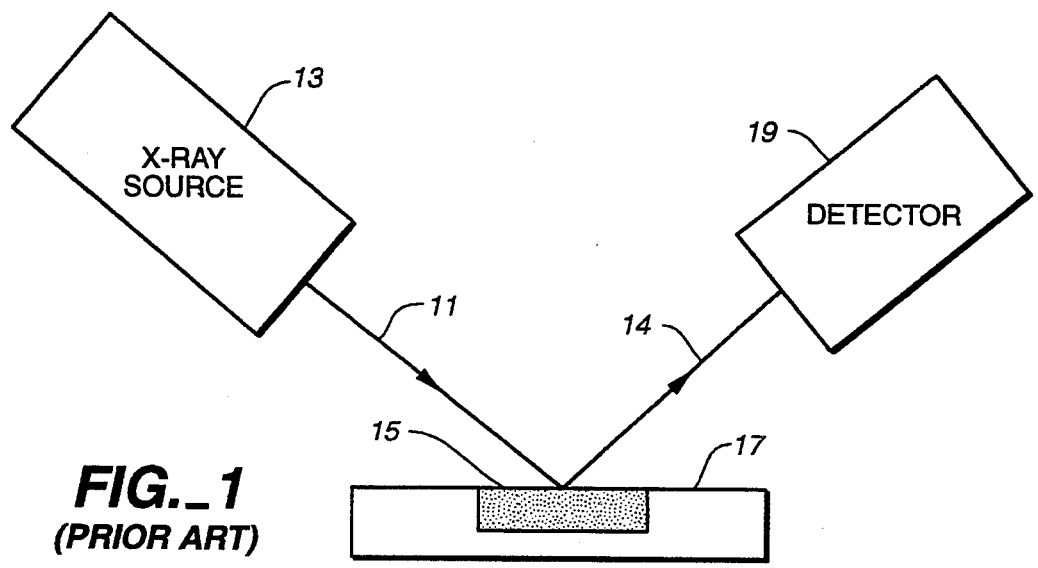
FIG._1
(PRIOR ART)
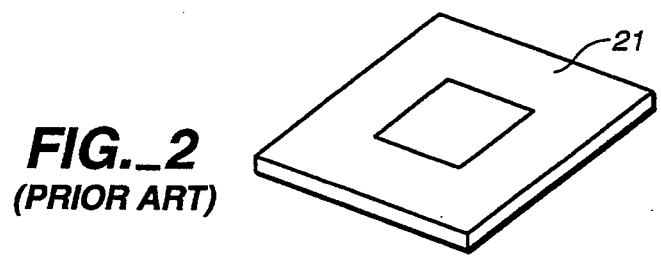
FIG._2
(PRIOR ART)
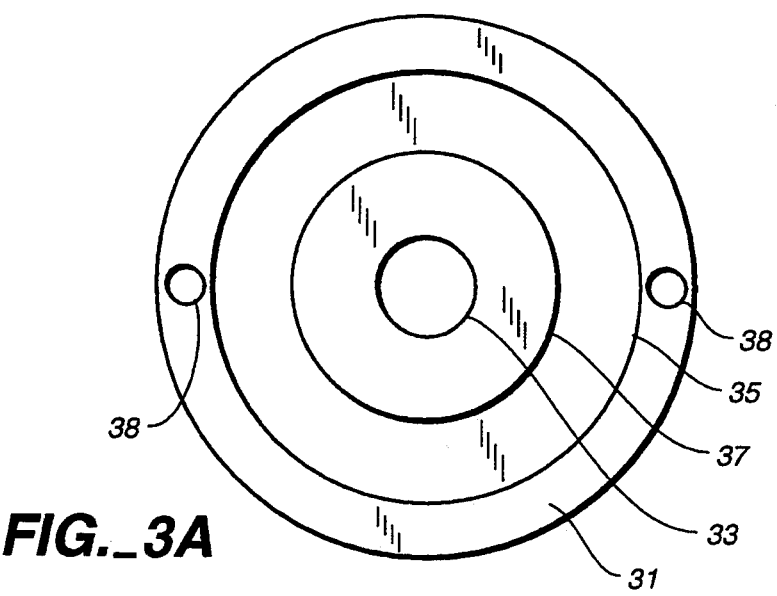
FIG._3A

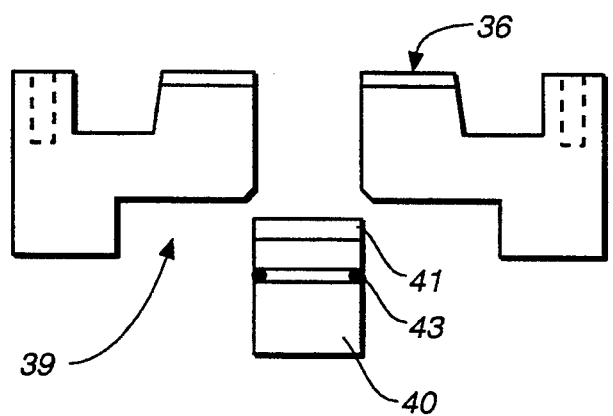
FIG._3B
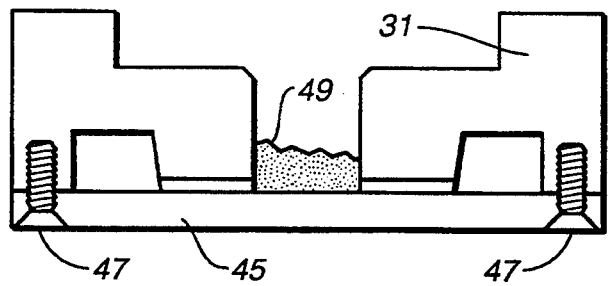
FIG._4A
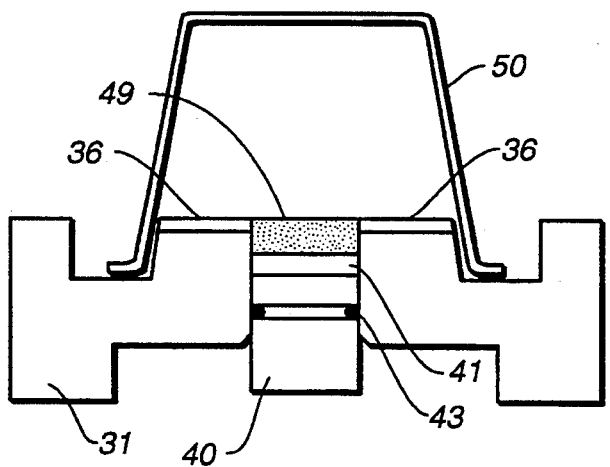
FIG._4B

CONTROLLED ATMOSPHERE, VARIABLE VOLUME SAMPLE HOLDER FOR X-RAY DIFFRACTOMER

BACKGROUND OF THE INVENTION

1. Field of the Invention

The present invention relates to the analysis of substances using electromagnetic radiation, and more particularly to a sample holder for X-ray diffractometry.

2. State of the Art

X-ray diffractometry, using the phenomenon of X-ray diffraction, is a well-known technique for performing physical and chemical analysis of crystalline substances. In X-ray diffraction, the crystal lattice of the crystalline substance acts in relation to X-rays in an equivalent manner as a diffraction grating acts in relation to visible light. Each unit cell of which a crystalline structure is composed acts as a diffraction center. The radiation intensity at a point removed from the crystalline structure is determined by the phase difference and intensity of radiation diffracted from each diffraction center to the point in question. A diffracted X-ray beam is essentially a collection of a large number of scattered X-ray waves that satisfy the conditions of constructive interference. These conditions are specified by Bragg's law, which may be stated as $2d = \lambda \sin\theta$ where d is the interplanar spacing of unit cells, $\lambda$ is the X-ray wavelength, and $\theta$ is the angle between the X-ray waves and a diffraction plane.

X-ray diffraction analysis may be performed on either single crystal substances or on crystalline powders. In a typical X-ray diffraction analysis, a powder sample is placed in a sample holder. The sample holder may be "front loading" or "back loading". A front loading sample holder is usually simply a plate with a depression at the center. The depression is filled with sample and excess sample is removed by scraping. A back loading sample holder is usually a plate with a large hole drilled through at the center. The hole is filled completely with sample powder from the backside, and a backplate is placed on the backside. The holder is then up-righted, and the front plate is removed to expose the sample. It is generally recognized that the back loading sample holder is effective in preventing preferred particle orientation, which is undersiderable, since X-ray diffractometry assumes that the crystals of a powder sample are randomly oriented.

During analysis, as shown in FIG. 1, the sample is irradiated with an X-ray beam 11 produced by an X-ray source 13 and incident at an angle. The X-ray 14 diffracted by the sample 15 held in the sample holder 17 is detected by a detector 19 positioned at a diffracted angle equal to the incident angle. The incident angle and hence the diffracted angle are incrementally varied as both the X-ray source 13 and the detector 19 move (in the plane of the figure) along a semicircle above the sample. The movements are synchronized so that the incident angle and the diffraction angle are always equal. The X-ray diffractometer records a diffractogram, which is the intensity of the diffracted X-ray as a function of angle. The sample can be identified based on its diffractogram.

A conventional front loading powder holder 21 is shown in FIG. 2. Commercially available sample holders are usually made of glass. There are also sample holders made of single crystal quartz in order to minimize background noise.

There are several disadvantages of most commercially available sample holders. First, the sample is exposed to air. A typical X-ray diffraction analysis may require from a few minutes to a few hours. To improve the signal-to-noise ratio of the detected signal, a large number of scans may be performed and signals detected at each scan added together. Air or moisture sensitive samples will be destroyed (chemically altered) during the analysis. One obvious way to protect the sample is to cover the sample with a metal or plastic film thin enough to allow the X-ray beam to pass through. The problem with this is that the film is also in the sampling point of the diffractometer. That is, X-rays diffracted by the sample cover will be detected by the X-ray detector. As a result, the background noise from the cover film cannot be distinguished from the signal of the sample.

Second, most commercially available sample holders are fixed-volume. Different sample holders must be used for samples of different size to achieve the best signal-to-noise ratio. To handle small samples, a sample holder with a small depression is necessary. But with a small depression, the area of the holder surrounding the sample, as well as the bottom of the depression, are also exposed to the X-ray beam. Unless the sample holder is made of specially prepared single crystal quartz, it will contribute to the background noise.

Accordingly, what is needed is an improved sample holder for diffraction analysis that protects air or moisture sensitive samples without degrading the detected signal. Furthermore, a sample holder is needed that accommodates samples of different sizes without contributing to background noise.

SUMMARY OF THE INVENTION

The present invention, generally speaking, provides a sample holder for diffraction analysis that protects air or moisture sensitive samples and accommodates samples of different sizes, both without contributing to background noise. In particular, a sample holder for beam diffractometery includes a holder body having a substantially flat beam-facing top surface and a through-hole extending through the top surface, a piston fitted in the through-hole so as to travel along an axis of the through-hole, and a cup-shaped cap fitted over at least a portion of the top surface, surrounding the through-hole. To minimize background noise, the top surface of the holder body and a top surface of the piston are made of quartz. For sample loading, a substantially flat plate and a mechanism for removably attaching the plate so as to overlie the top surface of the holder body are provided. The cap may be made of thin plastic so as to not affect the incident X-ray beam.

BRIEF DESCRIPTION OF THE DRAWINGS

The present invention may be further understood from the following description in conjunction with the appended drawings. In the drawings:

FIG. 1 is a block diagram of a conventional X-ray diffractometry set-up;

FIG. 2 is a perspective view of a conventional front loading sample holder;

FIG. 3A is a top view of the sample holder of the present invention;

FIG. 3B is a cross-sectional view of the sample holder of the present invention;

FIG. 4A is a cross-sectional view of the sample holder of the present invention in a loading position; and FIG. 4B is a cross-sectional view of the sample holder of the present invention in an analyzing position.

DETAILED DESCRIPTION OF THE PREFERRED EMBODIMENT

Referring now to FIGS. 3A and 3B, a body 31 of the present sample holder is formed of a thick disk, having a hole 33 drilled at the center. Aluminum has been found to be a suitable material for the disk, although other materials may also be used. A recess 35 is provided in the top surface of the holder 31 such that a portion 37 of the top surface surrounding the through hole is featured in surface relief. A plastic cap (not shown) may then be tightly fitted over this portion of the holder with the mouth of the plastic cap accommodated in the recess 35. To ensure low background noise, the portion 37 of the top surface surrounding the through hole is faced with a single crystal quartz plate 36 (FIG. 3B). A recess 39 is also provided in the bottom of the holder 31 to allow for a piston 40 to be manually inserted into the through hole 33, providing clearance for the piston 40 to be gripped using the thumb and the first two fingers. The piston, like the disk 31, may be made of aluminum.

A pair of threaded holes 38 near the edge along a diameter of the disk provide for attachment of a front plate during loading of the sample.

The piston 40 is approximately the same diameter as the through hole 33 and has a height somewhat less than the thickness of the disk of the sample holder 31. A single crystal quartz plate is attached to the top surface of the piston. Suitable quartz plate is available from the Gem Dug Out (State College, Pa.) The quartz plates are glued to the metal parts with an adhesive. An O-ring is fitted in a groove around the circumference of the piston so as to provide a friction fit of the piston inside the through hole. The grip end of the piston may be knurled to provide a better grip.

When used for air sensitive samples, the holder is loaded in a glove box with an inert atmosphere. The piston 40 is removed from the holder 31. As seen in FIG. 4A, a front plate 45 is attached to the front side of the holder with screws 47. The holder is inverted so the backside is facing up. The holder is then loaded with sample 49 from the backside. The piston 40 is replaced and pushed in until it stops. If desired, compression of the sample can be achieved with a press.

The holder 31 is then placed in the upright position (FIG. 4B). The front plate is removed. A plastic cap 50 is placed over the sample on the holder. Grease may be applied at the rim of the cap to improve the seal between the cap and the sample holder body. The cap is a disposable plastic beaker of a type available from VWR Scientific (San Francisco, Calif.). The holder with the sample can now be removed from the glove box and the sample can be analyzed.

The material of the plastic cap 50 has to be thin enough to allow X-ray beams to pass through it. A thickness of the plastic cap of about 1.5 mil has been found to be satisfactory, although a thicker cap may be more efective in keeping moisture away from the sample. A thicker cap may be expected to produce greater X-ray attenuation. Regardless of its thickness, the plastic cap does not contribute to background noise because no part of it is at the sampling point of the diffractometer. Low background noise is achieved by using single crystal quartz on the top surface of the holder.

Because the piston can be inserted at different depths, variable size samples can be handled. Low background noise is achieved by using single crystal quartz on the top surface of the piston.

EXAMPLE 1

X-ray diffraction analysis of KCl was performed on a Siemens D5000 X-ray diffractometer using the following settings:

Amplification=2
High voltage=850 V
Base level=0.460
Upper level=1.600
Tube voltage=50 KV
Tube current=35 mA A first diffractogram was obtained with the KCl powder in the sample holder not covered but exposed. KCl is not hygroscopic. Three scans were performed with each scan being approximately 1 minute in duration.

A KCl powder sample was then covered with a layer of polypropolene film (approximately 1 mil thick and a diffraction analysis was performed). Because the X-ray beam is incident at a glancing angle, the actual path length of the X-ray beam within the polypropolene film varies with the angle of incidence. Because the polypropolene film is positioned within the sample point of the diffractometer, extraneous peaks attributable to the polypropolene film were observed in the resulting diffractogram.

KCl powder was then loaded in the sample holder with the plastic cap over the sample. The resulting diffractogram was essentially the same as that of the exposed KCl. Unlike the polypropolene film, the plastic cap did not produce extraneous peaks in the diffractogram.

EXAMPLE 2

X-ray diffraction analysis was performed of LiCl, a hygroscopic compound which absorbs moisture from the atmosphere, forming a hydrated form of LiCl, possibly $LiCl.H_2O$. LiCl was loaded into the sample holder in a dry box. The cap was placed on the sample. The sample was analyzed after different periods of waiting time. Four scans were performed, each approximately a minute in duration, using the previously described settings. With the sample capped and analysis beginning at time t=0, a small peak was observed at a d-spacing of 2.716 Å and an angle of about 33°. In subsequent diffractograms taken at 10, 20 and 45 minutes, respectively, this peak grew perceptibly, indicating that moisture was being slowly absorbed through the imperfect seal between the cap and the sample holder. Diffractograms were then taken at 50, 55, 60 and 75 minutes, respectively, first removing the cap. The same line was then observed to peak dramatically, indicating that moisture was rapidly absorbed following removal of the cap as LiCl was converted to its hydrated form.

The foregoing has described the principles, preferred embodiments and modes of operation of the present invention. However, the invention should not be construed as limited to the particular embodiments discussed. Instead, the above described embodiments should be regarded as illustrative rather than restrictive, and it should be appreciated that variations may be made in those embodiments by workers skilled in the an without departing from the scope of the present invention as defined by the following claims.

What is claimed is:

1. A sample holder for beam diffractometry, comprising:
    a holder body having a substantially flat beam-facing top surface and a through-hole, extending through said top surface;
    a piston fitted in said through-hole so as to travel along an axis of said through-hole;
    a substantially flat plate;
    means for removably attaching said plate so as to overlie said through-hole and said flat beam-facing top surface; and
    a cup-shaped cap fitted over at least a portion of said top surface surrounding said through-hole.

2. The apparatus of claim 1 wherein said portion of said top surface is made of single crystal quartz.

3. The apparatus of claim 2 wherein a top surface of said piston is made of single crystal quartz.

4. The apparatus of claim 1 wherein said cap is removable.

5. The apparatus of claim 4 wherein said cap is made of thin plastic.

6. The apparatus of claim 1 further comprising an O-ring fitted about said piston so as to produce a friction fit between said piston and said through-hole.

7. A method of loading a back-loading sample holder for beam diffractometry, comprising the steps of:
    inverting the sample holder such that a backside of the sample holder is facing up;
    filling a through-hole in the sample holder with a sample to be analyzed;
    inserting a piston in the through-hole;
    moving the piston through the through-hole toward a flat plate removably mounted to a frontside of the sample holder;
    placing the sample holder in an upright position such that the frontside is facing up; and
    removing the front plate whereby the sample to be analyzed is exposed.

8. The method of claim 7, further comprising compressing the sample against the front plate with the piston.

9. The method of claim 7, further comprising placing a removable cup-shaped cap over the sample on the sample holder.

* * * * *